(12) United States Patent
Kenzari et al.

(10) Patent No.: US 11,054,374 B2
(45) Date of Patent: Jul. 6, 2021

(54) METHOD OF AUTHENTICATING AN OBJECT WITH X-RAY DIFFRACTION

(71) Applicant: CENTRE NATIONAL DE LA RECHERCHE SCIENTIFIQUE, Paris (FR)

(72) Inventors: Samuel Kenzari, Andilly (FR); Vincent Fournée, Laitre-sous-Amance (FR)

(73) Assignee: CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 17 days.

(21) Appl. No.: 16/629,716

(22) PCT Filed: Jul. 11, 2018

(86) PCT No.: PCT/EP2018/068790
§ 371 (c)(1),
(2) Date: Jan. 9, 2020

(87) PCT Pub. No.: WO2019/011986
PCT Pub. Date: Jan. 17, 2019

(65) Prior Publication Data
US 2020/0256810 A1  Aug. 13, 2020

(30) Foreign Application Priority Data

Jul. 11, 2017  (EP) .................................... 17305914

(51) Int. Cl.
*G01N 23/20*  (2018.01)
*G01N 33/204*  (2019.01)
*G06K 7/10*  (2006.01)

(52) U.S. Cl.
CPC ........... *G01N 23/20* (2013.01); *G01N 33/204* (2019.01); *G06K 7/1099* (2013.01)

(58) Field of Classification Search
CPC .............................. G01N 23/20; G01N 33/204
See application file for complete search history.

(56) References Cited

U.S. PATENT DOCUMENTS

2005/0112360 A1  5/2005  Berger et al.
2007/0071951 A1  5/2007  Grande et al.
(Continued)

FOREIGN PATENT DOCUMENTS

DE   692 23 180 T2   4/1998
WO   2012/174232 A2  12/2012

OTHER PUBLICATIONS

International Search Report from Corresponding International Application No. PCT/EP2018/068790 dated Sep. 11, 2018.
(Continued)

*Primary Examiner* — Edwin C Gunberg
(74) *Attorney, Agent, or Firm* — Pearne & Gordon LLP

(57) ABSTRACT

The application concerns a method of authenticating an object, the object comprising an identification substance including at least one amorphous phase, at least one crystalline phase and at least one complex metallic phase. The method includes the steps of: subjecting the identification substance of a candidate object to XRD analysis to determine an XRD signature thereof; comparing the XRD signature of the candidate object to a reference XRD signature, and concluding to the authenticity of the object when its XRD signature substantially matches the reference XRD signature.

22 Claims, 1 Drawing Sheet

(56) References Cited

U.S. PATENT DOCUMENTS

2007/0121181 A1    5/2007  Moon et al.
2014/0119511 A1    5/2014  Ward et al.

OTHER PUBLICATIONS

Written Opinion from Corresponding International Application No. PCT/EP2018/068790 dated Sep. 11, 2018.
Yu Ping Zhang; "Anti-counterfeiting method using synthesized Nanocraystalline Cellulose Taggants"; Nov. 21, 2012; XP055423442; Retrieved from the Internet: URL:http://digitool.library.mcgill.ca/webclient/StreamGate?folder_id=0&dvs=1510241185817 742.

a)
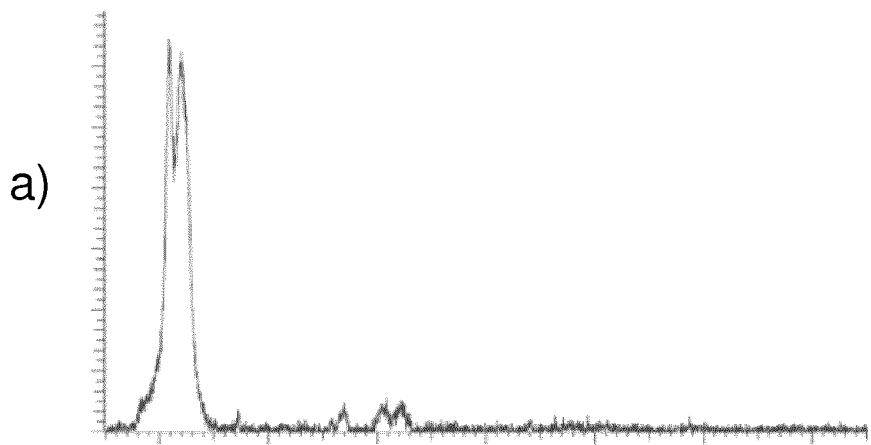
b)
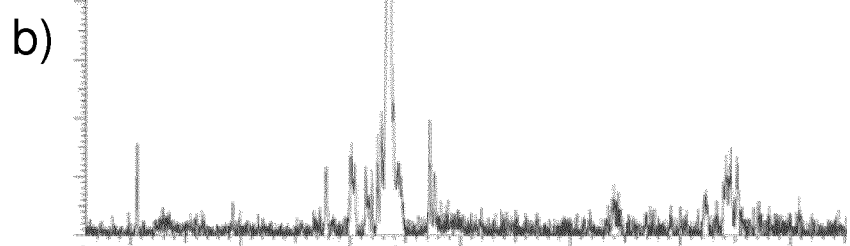
c)
d)
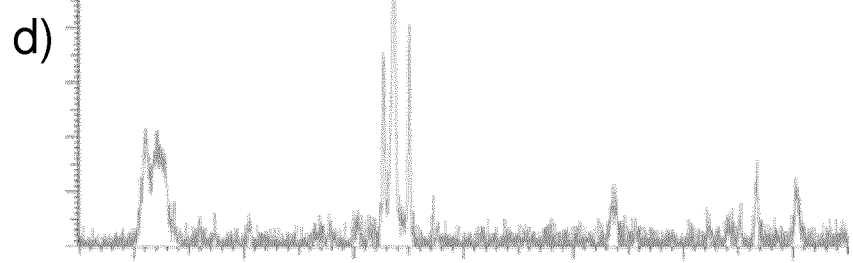

METHOD OF AUTHENTICATING AN OBJECT WITH X-RAY DIFFRACTION

FIELD OF THE INVENTION

The present invention generally relates to a method of authenticating objects such as goods, products, articles, materials, etc. in order to avoid counterfeited objects. More specifically, the present invention relates to a method of authenticating objects based on X-ray diffraction analysis.

BACKGROUND OF THE INVENTION

Counterfeiting is a longstanding problem that is growing in scope and magnitude. Counterfeiting is a concern to businesses because of the impact that it has on sales, brand value and a firm's reputation, as well as on the ability to benefit from technical innovations. Consumers are of course also victims of counterfeiting, being defrauded of the genuine product they have paid for and, with regard to e.g. goods such as mechanical parts or drugs, running significant health and safety risks. At State level, counterfeiting is a concern for governments because of the threat it poses to the welfare and health of consumers, the negative impact it can have on innovation, and the substantial resources channeled to criminal networks, organized crime and other groups that disrupt and corrupt society.

Today, there are a multitude of technologies that can be used in the fight against counterfeit goods. For example, nano and other advanced technologies are opening the door to new ways of brand protection, product tracking and tracing: it offers the potential for uniquely 'fingerprinting' the actual product (without affecting it), as well as the packaging. In this connection, the report "*Nano and other Innovative Anti-Counterfeit Technologies*", published by the Technology Transfer Centre in April 2016, describes over 40 very exciting, and in the main, very recent (mostly reported between 2014-2016) solutions.

Current anti-counterfeiting technology options comprise a range of overt and covert measures which encompass product authentication and security. The anti-counterfeiting market can be mainly categorized into two segments, namely authentication technologies (the technologies providing overt and covert security features); and Track & Trace Technologies (the technologies facilitating visibility of products throughout the supply chain).

These technology options include serial numbers, barcodes, datamatrix and RFID for identification, and holograms, biometric solutions, watermarks and taggants for security. These technologies have their own limitations at different levels and are not foolproof.

One particular challenge of anti-counterfeiting measures is the difficulty to prevent copying of the RFID device, taggant, hologram or other fingerprint.

US 2007/0121181 discloses a method of labeling and identifying an item based on X-ray diffraction (XRD) analysis. The method employs an optical identification element formed by powdered crystal materials in a binder to provide a composite X-ray diffraction pattern when illuminated by an X-ray beam. The composite X-ray diffraction pattern is indicative of the item. The method further relies on the use of a composite X-ray diffraction pattern "encoded" by the selection and omission of one or more of the four different crystalline materials.

The optical identification element can be given a variety of shapes (beads, cylinders, fibers) and may be used for many different purposes, such as for sorting, tracking, identification, verification, authentication, anti-theft/anti-counterfeit, security/anti-terrorism, or for other purposes.

The proposed method is of interest since it allows for a large number of distinct codes, can be made very small, signature is readable independent of orientation, can withstand harsh environments.

Despite these advantages, the method disclosed in US 2007/0121181 does not appear to be safe enough. Indeed, XRD is a standard way of detecting crystalline materials. It would be relatively easy for skilled persons to analyze the optical identification element to detect the different crystalline materials and reproduce a compound with very similar or identical X-ray diffraction pattern. Other methods of authenticating objects are e.g. known from WO 2012/174232, US 2005/0112360, US 2007/0071951 or Yu Ping Zhang in "Anti-counterfeiting method using synthesized Nanocrystalline Cellulose Taggants", 21 Nov. 2012, Ph.D Thesis McGill University, Montreal.

OBJECT OF THE INVENTION

The object of the present invention is to provide an improved method of identifying an object based on XRD analysis, which provides a unique XRD fingerprint that is difficult to copy.

This object is achieved by a use as claimed in claim 1 and a method as claimed in claim 2 or 5.

SUMMARY OF THE INVENTION

The present invention exploits the properties of quasicrystals and approximant metallic alloys in combination with an amorphous and/or crystalline phase to provide an improved method of authenticating articles by X-ray diffraction (XRD) analysis.

According to a first aspect, the present invention proposes the use of a substance or compound, hereinafter referred to as identification substance, comprising at least one amorphous phase, at least one crystalline phase and at least one complex metallic phase in a method for authenticating an object by analysis of an X-Ray diffraction signature of the compound.

According to a second aspect, a method of identifying an object is proposed, wherein the object comprises an identification substance including at least one amorphous phase, at least one crystalline phase and at least one complex metallic phase. The method comprises:
- subjecting the identification substance of a candidate object to XRD analysis to determine an XRD signature thereof;
- comparing the XRD signature of the candidate object to a reference XRD signature, and concluding to the authenticity of the object when its XRD signature substantially matches the reference XRD signature.

A characteristic feature of the present invention is thus the use of an identification substance including a combination of at least one amorphous phase, at least one crystalline phase and at least one complex metallic phase. Such identification substance has a unique diffraction pattern that constitutes a unique signature or fingerprint, and its composition cannot be determined after manufacturing. It should be appreciated that there is no available analysis techniques today that would allow precisely determining the nature and quantities of the respective constituents. In particular, chemical analysis does not allow deciphering the composition providing a given characteristic X-ray diffraction pattern; it simply identifies the different elements without distinguishing the structures and relations between the different crystallographic phases.

XRD analysis is also unable to determine the compositions of such identification substance, since it does not allow identifying the respective volume fractions of each phase.

Remarkably, as will be seen in more detail below, the X-ray absorption phenomena and overlapping of the diffraction peaks of the different crystalline and complex metallic alloy phases make it impossible to precisely determine the various volume fraction of the different phases constituting the identification substance.

However, the present identification substance can be readily manufactured using existing technologies and authenticated by XRD analysis. Upon manufacture of the substance, a sample thereof is stored, or simply its XRD signature is stored as reference signature. Authentication of a candidate material or substance can thus be made by comparing its XRD signature to the reference XRD signature.

The uniqueness of the XRD signature and impossibility of copying the specified compounds result in a strong and safe authentication method that can be used with goods and products requiring a visible or non-visible protection.

The identification substance can be given a variety of shapes (beads, cylinders, fibers) and may be used for many different purposes, such as for sorting, tracking, identification, verification, authentication, anti-theft/anti-counterfeit, security/anti-terrorism, or for other purposes.

In practice, a batch of the identifying material (i.e. comprising at least one amorphous phase, at least one crystalline phase and at least one complex metallic phase) can be manufactured and used for production of, or used as, any kinds of markers, e.g. labels or taggants, that can be associated with an object for authentication purposes. An amount of the identification substance, in any appropriate form, is thus directly applied to the object (i.e. physically associated), or linked thereto or affixed to a notice, label or packaging.

It is also possible to integrate an amount of the identification substance in the bulk of the object or make it integral therewith. Also, the object can be integrally or partly manufactured from the identification substance, or a component of the object can be manufactured from the identification substance.

There is thus a variety of ways of combining the identification substance with the object to be authenticated.

Basically, the identification substance is manufactured and an XRD analysis is made therefrom, which will serve as reference XRD signature.

The term "XRD signature" is used herein to designate at least a part of the XRD diffraction pattern measured for a reference identification substance or a candidate that contains characteristic values of the XRD pattern. The XRD signature can be stored graphically or as a data set; also, only a part, or some parts, of the XRD pattern may be used for authentication purposes. In practice, the XRD signature preferably comprises a characteristic set of angles and intensity values representative of the analysed sample.

The step of comparing the measured XRD signature (i.e. for the candidate sample) to the reference sample thus consists in comparing the correspondence of the respective XRD signatures (graphically or numerically). The candidate and reference XRD signatures are considered to match when the angular positions of the peaks and intensities correspond exactly or are within a certain tolerance range. Hence, the comparison step will mainly involve comparing angular positions of representative/characteristic peaks and/or comparing relative intensities between representative/characteristic peaks.

For ease of calibration, the identification substance preferably comprises a known calibration crystal, such as e.g. a silicon. This will allow precise positioning along the x axis (theta) of the diffraction diagram.

According to a third aspect, the invention concerns a method of authenticating an object, which comprises the steps of:

a) manufacturing an identification substance including at least one amorphous phase, at least one crystalline phase and at least one complex metallic phase;
b) subjecting an amount of the identification substance to XRD analysis to determine an XRD signature thereof and storing the latter as reference XRD signature;
c) associating an amount of the identification substance to an object;
d) subjecting a candidate identification substance associated with an object to be identified to XRD analysis to determine an XRD signature thereof;
e) comparing the XRD signature of the candidate identification substance to the reference XRD signature, and concluding to the authenticity of the object to be identified when its XRD signature substantially matches the reference XRD signature.

In this method, smaller or larger batches of identification substance are formed and the XRD signature of the obtained substance is stored as reference for future authentication purposes. The identification substance is used to manufacture markers, labels, taggants of any appropriate form.

For example, a plurality of labels or taggants may be manufactured from the identification substance and the labels are applied or tied to objects. The taggants may also be applied to labels or packaging of objects or can be directly applied to objects.

In embodiments, amounts of the identification substance are added to the bulk of objects to be authenticated, in particular during object production and/or packaging.

The present method can be easily implemented with present technologies. A variety of materials are available to provide the three required phases. X-ray diffraction analysis is a standard technology and any appropriate X-ray diffraction measurement system may be used. The sample substance to be analyzed does not need particular preparation. The obtained diffraction patterns and corresponding signatures can be stored on any computer readable support.

Also, the identification substance used in the present invention can be adapted and formed by means of any polymer technology, e.g. additive manufacturing, laser sintering, stereo-lithography, injection molding, resin casting, etc.

In this connection, to take advantage of polymer technologies which allow easy production of the identification substance, an amorphous or semi-crystalline polymer can be used as matrix, to which particles containing the other required phases are added. Preferably, powders and finer or coarser particulate material containing one or more crystalline phases and/or one or more complex metallic phases are selected and added to the polymer matrix according to predetermined amounts, depending on the desired mixture.

In the present specification, the term "amorphous phase" is used in its conventional meaning, generally designating non-periodic 3D structural arrangement, lacking the long-range order that is characteristic of a crystal. Typically, in an amorphous phase, X-rays will be scattered in many directions leading to only broad peaks characteristic of not well-defined short range order. Preferably, the amorphous phase is provided by a polymer.

In the present specification, the term "crystalline phase" is used in its classical crystallographic meaning, designating crystal structure, i.e. an ordered arrangement of atoms, ions or molecules, forming symmetric patterns that repeat periodically along the principal directions of the three-dimensional space in matter. As used herein, the term "crystalline phase" thus covers the historic definition of crystals, and does not encompass so-called "quasicrystals" or more generally "complex metallic alloys", as defined below. Crystalline phases have powder XRD patterns characterized by a finite set of sharp and intense diffraction peaks.

In the present specification, the term "complex metallic alloy" designates an alloy that is either a quasi-crystalline phase strictly speaking, or else so-called approximant phases. Quasi-crystalline phases in the strict sense are phases presenting forbidden rotational symmetries that are normally incompatible with translational symmetry characteristic of classical crystals: i.e. rotational symmetries of order 5, 8, 10, or 12. By way of example, mention may be made of the icosahedral phase with icosahedral group symmetry and the decagonal phase with decagonal point group symmetry.

Approximant phases or approximant compounds are true crystals insofar as their crystallographic structure remains compatible with translational symmetry with short range order similar to that of quasi-crystals, but in an electron diffraction shot they present diffraction patterns of symmetry close to symmetry of order 5, 8, 10, or 12. They are phases characterized by an elementary mesh containing several tens or even several hundreds of atoms, and in which local order presents arrangements of almost icosahedral or decagonal symmetry similar to the related quasi-crystalline phases. Complex metallic alloys have powder XRD characterized by a dense set of sharp and intense diffraction peaks, significantly more complex than regular metallic alloys.

Among these phases, mention may be made by way of example of the orthorhombic phase $O_1$, characteristic of an alloy of atomic composition $Al_{65}Cu_{20}Fe_{10}Cr_5$, having mesh parameters expressed in nanometers (nm) that are: $a_0^{(1)}=2.366$, $b_0^{(1)}=1.267$, $c_0^{(1)}=3.252$. This orthorhombic phase $O_1$ is said to be approximant to the decagonal phase. The nature of the two phases can be identified by transmission electron microscopy.

Mention may also be made of the rhombohedral phase having the parameters $a_R=3.208$ nm, $\alpha=36°$, that is present in alloys of atomic composition close to $Al_{64}Cu_{24}Fe_{12}$. This phase is an approximant phase of the icosahedral phase.

Mention may also be made of the orthorhombic phases $O_2$ and $O_3$ having respective parameters in nm: $a_0^{(2)}=3.83$, $b_0^{(2)}=0.41$, $c_0^{(2)}=5.26$; and $a_0^{(3)}=3.25$, $b_0^{(3)}=0.41$, $c_0^{(3)}=9.8$, that are present in an alloy of atomic composition $Al_{63}Cu_{17.5}Co_{17.5}Si_2$, or indeed the orthorhombic phase $O_4$ having parameters in nm of: $a_0^{(4)}=1.46$, $b_0^{(4)}=1.23$, $c_0^{(4)}=1.24$ that forms in the alloy of atomic composition $Al_{63}Cu_8Fe_{12}Cr_{17}$.

Mention may also be made of a phase C of cubic structure that is observed very often to coexist with approximant or true quasi-crystalline phases. This phase, which forms in certain Al—Cu—Fe and Al—Cu—Fe—Cr alloys, consists in a superstructure, by a chemical, order effect of the elements of the alloy relative to the aluminum sites, of a phase having a structure of Cs—Cl type and a lattice parameter $a_1=0.297$ nm.

Mention may also be made of a phase H of hexagonal structure that is derived directly from the phase C as demonstrated by the epitaxial relationships observed by electron microscope between crystals of phases C and H and the simple relationships that link together the parameters of crystal lattices, namely $aH=3\sqrt{a_1}/\sqrt{3}$ (to within 4.5%) and $cH=3\sqrt{2} \cdot a_1/2$ (to within 2.5%). This phase is isotypical of a hexagonal phase, written $\phi AlMn$, that is found in Al—Mn alloys containing 40% by weight Mn.

The cubic phase, its superstructures, and the phases that derive therefrom, constitute a class of approximant phases of quasi-crystalline phases of similar compositions.

Also for example, quasi-crystalline alloys of the Al—Cu—Fe system are appropriate for use in the method according to the present invention.

Mention may be made in particular of the alloys having any one of the following atomic compositions: $Al_{62}Cu_{25.5}Fe_{12.5}$, $Al_{59}Cu_{25.5}Fe_{12.5}B_3$, $Al_{71}Cu_{9.7}Fe_{8.7}Cr_{10.6}$, and $Al_{71.3}Fe_{8.1}Co_{12.8}Cr_{7.8}$. These alloys are manufactured by Saint-Gobain (France). In particular, the $Al_{59}Cu_{25.5}Fe_{12.4}B_3$ alloy is sold under the name Cristome F1, the $Al_{71}Cu_{9.7}Fe_{8.7}Cr_{10.6}$ alloy is sold under the name Cristome A1, and the $Al_{71.3}Fe_{8.1}Co_{12.8}Cr_{7.8}$ alloy is sold under the name Cristome BT1. Cristome F1, A1 and BT1 are only cited as examples and should not be construed as limiting.

Complex metallic alloys for use in the present invention may be metallic alloys comprising an atomic percentage of aluminum that is greater than 50%.

As explained above, the present invention relies on the use of a unique composite XRD signature of an identification substance comprising a mixture of at least the three following phases: an amorphous phase, a crystalline phase and a complex metallic phase.

Conveniently, the amorphous phase is provided by an amorphous material, in particular a polymer. The identification substance can be produced by adding solid particles to the amorphous material to form the at least one crystalline phase and at least one complex metallic phase.

Suitable amorphous materials are e.g. amorphous or semi-crystalline polymers, elastomers, glass, metallic glass.

As for the crystalline materials, any appropriate crystalline solids may be used. Metals and metallic alloys are particularly suitable.

During manufacture of the identification substance, the different components forming the respective phases are mixed in given quantities, leading to respective volumes fractions of each phase. The XRD signature of such identification substance is unique and specific to the material as prepared, since its XRD diffraction pattern is function of the respective volume fractions of the phases present in the identification substance. Due to the use of complex and approximant phase materials, the material cannot be reproduced or copied without knowledge of the starting composition (i.e. the initial materials and respective amounts).

The appended FIG. 1 illustrates the complexity of the XRD signature of the identification substance used in the present authentication method. The first three XRD patterns correspond respectively to the following components of the identification substance:

a) a semi-crystalline polymer containing an amorphous phase and a crystalline phase. Here the principal peak is due to the crystalline phase.
b) an approximant metallic alloy containing two crystalline phases.
c) a complex metallic alloy containing 1 crystalline phase and 1 quasi-crystalline phase.

The polymer typically forms the matrix, in which the metallic alloys forming the other phases are added as powders, fine or coarse particles, or any appropriate shape.

In the above example, the semi-crystalline polymer (here polyamide 12), represents 50 percentage by mass (m %); the approximant metallic alloy 25 m % and the complex metallic alloy 25 m %. The approximant and complex metallic alloys were alloys of the Al—Cu—Fe system with appropriate additions (Chromium or Boron, as explained above).

The XRD pattern of the composite material obtained by mixing these three materials in the indicated amounts, to form the identification substance, is shown in FIG. 1 d). As can be seen, the six phases present in the individual materials combine to provide a non-predictable diffraction pattern.

It may be noted that there is an absorption phenomenon that leads to a small polymer peak, although the polymer is a majority constituent in terms of mass and volume. This adds to the difficulty of deciphering the composition.

It shall be appreciated that the X-ray absorption phenomena and overlapping of the diffraction peaks of the different crystalline and complex metallic alloy phases make it impossible to precisely determine the various volume fraction of the different phases constituting the identification substance.

Accordingly, the XRD pattern of FIG. 1 d) is considered to form a unique signature or fingerprint that cannot be reproduced, since it is not possible to determine the volume fractions of the respective phases. The identification substance/composite cannot be reproduced without knowledge of the initial recipe, i.e. the respective constituents and their amounts.

The invention claimed is:

1. A method of authenticating an object, the object comprising an identification substance including at least one amorphous phase, at least one crystalline phase and at least one complex metallic phase, said method comprising:
    subjecting the identification substance of a candidate object to X-Ray diffraction, XRD, analysis to determine an XRD signature thereof;
    comparing the XRD signature of the candidate object to a reference XRD signature, and concluding to the authenticity of the object when its XRD signature substantially matches the reference XRD signature.

2. The method according to claim 1, wherein said identification substance is formed as a label or taggant associated with said object or directly applied on said object.

3. The method according to claim 1, wherein said object is manufactured from said identification substance, at least in part; or said identification substance is in the bulk of or integral with said object.

4. The method as claimed in claim 1, wherein said identification substance comprises at least one polymer with an amorphous phase, said at least one polymer preferably forming a matrix of said identification substance.

5. The method as claimed in claim 1, wherein said identification substance comprises a metallic alloy with at least one approximant metallic phase.

6. The method as claimed in claim 1, wherein said identification substance comprises a metallic alloy with at least one quasi-crystalline phase.

7. The method as claimed in claim 1, wherein said identification substance comprises a polymer matrix with at least one amorphous phase with embedded particles of a complex metallic alloy comprising at least one crystalline phase and at least one complex metallic phase.

8. The method as claimed in claim 1, wherein said comparison step comprises comparing angular positions of relevant peaks between the candidate XRD signature and the reference XRD signature.

9. The method as claimed in claim 1, wherein said comparison step comprises comparing relative intensities of relevant peaks between the candidate XRD signature and the reference XRD signature.

10. The method as claimed in claim 1, wherein said identification substance comprises a predetermined calibration crystal comprises silicon.

11. A method of authenticating an object, said method comprising the steps of:
    a) manufacturing an identification substance including at least one amorphous phase, at least one crystalline phase and at least one complex metallic phase;
    b) subjecting an amount of said identification substance to X-Ray diffraction, XRD, analysis to determine an XRD signature thereof and storing the latter as reference XRD signature;
    c) associating an amount of said identification substance to an object;
    d) subjecting a candidate identification substance associated with an object to be identified to XRD analysis to determine an XRD signature of said identification substance;
    e) comparing said XRD signature of said candidate identification substance to said reference XRD signature, and concluding to the authenticity of said object to be identified when its XRD signature substantially matches said reference XRD signature.

12. The method according to claim 11, wherein a plurality of labels or taggants are manufactured from said identification substance and said labels are applied or tied to objects.

13. The method according to claim 11, wherein amounts of said identification substance are applied to labels or packaging of objects or are applied directly to objects.

14. The method according to claim 11, wherein amounts of said identification substance are added to the bulk of objects to be authenticated during object production and/or packaging.

15. The method as claimed in claim 11, wherein said identification substance comprises at least one polymer with an amorphous phase, said at least one polymer preferably forming a matrix of said identification substance.

16. The method as claimed in claim 11, wherein said identification substance comprises a metallic alloy with at least one approximant metallic phase.

17. The method as claimed in claim 11, wherein said identification substance comprises a metallic alloy with at least one quasi-crystalline phase.

18. The method as claimed in claim 11, wherein said identification substance comprises a polymer matrix with at least one amorphous phase with embedded particles of a complex metallic alloy comprising at least one crystalline phase and at least one complex metallic phase.

19. The method as claimed in claim 11, wherein said comparison step comprises comparing angular positions of relevant peaks between the candidate XRD signature and the reference XRD signature.

20. The method as claimed in claim 11, wherein said comparison step comprises comparing relative intensities of relevant peaks between the candidate XRD signature and the reference XRD signature.

21. The method as claimed in claim 11, wherein said identification substance comprises a predetermined calibration crystal comprising silicon.

22. An authentication method comprising analysing an X-Ray diffraction signature of an identification substance, wherein said identification substance comprises at least one amorphous phase, at least one crystalline phase and at least one complex metallic phase.

\* \* \* \* \*